United States Patent [19]

Mihalovits

[11] 4,369,180

[45] Jan. 18, 1983

[54] COSMETIC FACIAL PREPARATION CONTAINING ALOE VERA

[75] Inventor: Donna M. Mihalovits, Atlanta, Ga.

[73] Assignee: Randolph C. Karrh, Swainsboro, Ga. ; a part interest

[21] Appl. No.: 300,992

[22] Filed: Sep. 10, 1981

[51] Int. Cl.³ .................. A61K 37/00; A61K 31/595; A61K 31/365; A61K 35/78

[52] U.S. Cl. .................................. 424/177; 424/195; 424/237; 424/359

[58] Field of Search ............... 424/195, 237, 359, 177

[56] References Cited

U.S. PATENT DOCUMENTS 3,878,197  4/1975  Maret ................................. 424/195
4,201,235  5/1980  Ciavatta ............................. 424/237
4,223,018  9/1980  Belle .................................. 424/177

OTHER PUBLICATIONS

Nature's Bounty, 1979, published by Nature's Bounty, Inc., Bohemia, N. Y., p. 42.

CTFA Cosmetic Ingredient Dictionary, 1973, 1st Ed., published by the C.T.F.A., Wash. D.C. pp. 7, 40, 44, 88, 108, 143, 160 and 188–189.

*Primary Examiner*—Donald B. Moyer
*Attorney, Agent, or Firm*—Rodgers & Rodgers

[57] ABSTRACT

A cosmetic facial preparation comprising aloe vera, cornstarch or cosmetic clay, albumin, allantoin, Vitamin A, Vitamin $D_2$ and Vitamin E.

4 Claims, No Drawings

COSMETIC FACIAL PREPARATION CONTAINING ALOE VERA

This invention relates generally to facial preparations which cleanse and soften the skin and improve its texture using a solution which contains aloe vera, cornstarch or cosmetic clay, albumin, allantoin, and Vitamins A, $D_2$ and E.

BACKGROUND OF THE INVENTION

Many solutions of differing compositions which are designed to be applied to the skin are known in the prior art. An example of a composition which cleanses the skin which includes Vitamins $D_2$ and A and protein is disclosed in U.S. Pat. No. 4,223,018 to Belle. A cosmetic oil including Vitamins A and D and olive oil is disclosed in U.S. Pat. No. 2,865,859 to Lubowe. A dermotological preparation for topical application to the skin combining protein, acid and vitamins is disclosed in U.S. Pat. No. 2,876,164 to Wershaw.

A juice or gel from the aloe vera leaf, a tropical plant, has long been used as topical treatment of the skin. U.S. Pat. No. 3,878,197 to Maret discloses a process for extracting and stabilizing aloe vera juice. U.S. Pat. No. 4,178,372 to Coats discloses a process for preparing a hypo-allergenic aloe vera gel.

However, none of the above prior art compositions have provided a lotion which cleanses and softens the skin and improves its texture and at the same time restores essential vitamins and proteins to the skin.

SUMMARY OF THE INVENTION

The present invention provides a novel cosmetic facial preparation for cleansing and softening the skin and improving its texture. In addition it restores vitamins and proteins to the skin.

An object of the invention is to provide a cosmetic preparation which contains vitamins and proteins to promote the health of the skin and which also cleanses, softens and improves the texture of the skin.

The cosmetic preparation comprising this invention contains the following ingredients and percentages by weight set forth:

| Ingredient | Minimum Percentage | Maximum Percentage |
| --- | --- | --- |
| Aloe Vera | 25 | 75 |
| Citric Acid | 0.2 | 2 |
| Potassium Sorbate | 0.1 | 2 |
| Sodium Benzoate | 0.1 | 2 |
| Cornstarch | 10 | 70 |
| Albumin | 1 | 10 |
| Hydroxypropyl-methylcellulose | 0.5 | 10 |
| Allantoin | 0.5 | 5 |
| Retinol (Vitamin A) | 0.1 | 5 |
| Ergocalciferol (Vitamin $D_2$) | 0.1 | 5 |
| Tocopherol (Vitamin E) | 0.1 | 5 |

Other features, objects and advantages of the present invention are stated in or apparent from the detailed description of a presently preferred embodiment of the invention found herein below.

DETAILED DESCRIPTION OF THE PREFERRED EMBODIMENT

The preparation of this cosmetic preparation using commercially available products is accomplished in the following manner. The liquid and dry ingredients of the cosmetic preparation are prepared separately and then mixed together. An aloe vera gel is converted into liquid form by heating at a low temperature under pressure. It is necessary that it be heated at a low heat in order for it to retain as many of the natural ingredients present as possible. Citric acid is added to the aloe vera concentrate to adjust the pH of the composition to within a range of from about 4 to about 6. Sodium benzoate and potassium sorbate are added to the liquid composition as stabilizers. This liquid composition consists of approximately 97.5% aloe vera, 1.5% citric acid, 0.5% potassium sorbate and 0.5% sodium benzoate. The concentrated liquid aloe vera prepared in this manner has a long shelf life.

A powder can be prepared in mixing the following ingredients together in the following percentages:

| | |
| --- | --- |
| Cornstarch | 75% |
| Albumin | 9% |
| Hydroxypropylmethyl-cellulose | 10% |
| Allantoin | 3% |
| Retinol (Vitamin A) | 1% |
| Ergocalciferol (Vitamin $D_2$) | 1% |
| Tocopherol (Vitamin E) | 1% |

The cornstarch and albumin are preferably mixed together first. The albumin can be added in the form of dried egg whites. The liquid form of Vitamin A has been found to mix satisfactorily with the powder. The liquid form of Vitamin $D_2$ also mixes well with the powder. The Vitamin $D_2$ may be in propolene glycol as a carrier and preferably contains approximately 8,000 units of ergocalciferol per gram. Hydroxypropylmethylcellulose is added as a thickener. Cosmetic clay can be used in lieu of cornstarch within the same percentage range as the cornstarch. Both cosmetic clay and cornstarch may be used with the minimum percentage of cornstarch in the preparation being about 0.5% with the maximum percentage being about 69.5% with the minimum percentage of cosmetic clay being about 0.5% with the maximum percentage being about 69.5%.

Preferably the powder portion and the liquid portion are mixed together in equal amounts partly before use. The two portions must be mixed together until the powder is completely dissolved and lump free.

Before this cosmetic preparation is applied, the skin should be thoroughly cleaned with a cleansing solution which is then removed with a damp cloth. A cosmetic preparation is then applied to the throat and face, preferably with a brush. The preparation is applied beginning at the base of the throat and working upward and outward until the throat and face are completely covered. The cosmetic preparation is allowed to harden (and allowed to remain on the face for approximately 30 minutes). The cosmetic preparation can then be removed using a wet warm cloth to soften the preparation. Upward gentle strokes are used so that the skin will tend to retain the configuration imparted by the preparation. It may be desirable to add moisture cream after the preparation has been removed to replenish any moisture which may have been removed from the skin.

This cosmetic preparation results in cleansing various impurities from the skin and leaves the skin firmer in texture and appearance and, in addition, refines pores. The skin may also show a marked color difference in that it is lighter. This is due to the cleansing action that has taken place. These changes in texture and appearance of the skin result in the person appearing to have had a face lift. These changes of course are not permanent and the person must periodically reapply the preparation. The skin may also be slightly flushed and pink due to stimulation of the preparation and its application, but this flushed appearance will usually dissipate within a few minutes. It is preferred that this cosmetic preparation be used three or four times in the first ten days of its use and then once every three or four weeks thereafter.

The following example illustrates a specific formulation that may be employed for the cosmetic preparation of the present invention.

| Example: | Percentage by Weight |
|---|---|
| Liquid Portion | |
| Aloe Vera | 48.75 |
| Citric Acid | 0.75 |
| Potassium Sorbate | 0.25 |
| Sodium Benzoate | 0.25 |
| Powder Portion | |
| Cornstarch | 37.5 |
| Albumin | 4.5 |
| Hydroxypropylmethylcellulose | 5.0 |
| Allantoin | 1.5 |
| Retinol | 0.5 |
| Ergocalciferol | 0.5 |
| Tocopherol | 0.5 |

As indicated above the liquid and powder portions are prepared separately and then mixed together in equal amounts. The preparation is applied to the throat and face with a brush using upward strokes. The solution is allowed to set for approximately thirty minutes and then removed with a wet washcloth.

What I claim is:

1. A cosmetic facial preparation comprising the following ingredients in the following percentages by weight in the final composition:

| Ingredient | Minimum Percentage | Maximum Percentage |
|---|---|---|
| Aloe Vera | 25 | 75 |
| Citric Acid | 0.2 | 2 |
| Potassium Sorbate | 0.1 | 2 |
| Sodium Benzoate | 0.1 | 2 |
| Cornstarch | 10 | 70 |
| Albumin | 1 | 10 |
| Hydroxypropylmethylcellulose | 0.5 | 10 |
| Allantoin | 0.5 | 5 |
| Vitamin A | 0.1 | 5 |
| Vitamin $D_2$ | 0.1 | 5 |
| Vitamin E | 0.1 | 5 |

2. Cosmetic preparation comprising the following ingredients expressed as a percent by weight: about 48.75% aloe vera; about 0.75% citric acid, about 0.25% potassium sorbate; about 0.25% sodium benzoate; about 37.5% cornstarch; about 4.5% albumin; about 5% hydroxypropylmethylcellulose; about 1.5% allantoin, about 0.5% Vitamin A; about 0.5% Vitamin $D_2$; and about 0.5% Vitamin E.

3. A cosmetic facial preparation comprising the following ingredients in the following percentages by weight in the final composition:

| Ingredient | Minimum Percentage | Maximum Percentage |
|---|---|---|
| Aloe Vera | 25 | 75 |
| Citric Acid | 0.2 | 2 |
| Potassium Sorbate | 0.1 | 2 |
| Sodium Benzoate | 0.1 | 2 |
| Cosmetic Clay | 10 | 70 |
| Albumin | 1 | 10 |
| Hydroxypropylmethylcellulose | 0.5 | 10 |
| Allantoin | 0.5 | 5 |
| [Retinol] Vitamin A | 0.1 | 5 |
| [Ergocalciferal] Vitamin $D_2$ | 0.1 | 5 |
| [Tocopherol] Vitamin E | 0.1 | 5 |

4. A cosmetic facial preparation comprising the following ingredients in the following percentages by weight in the final composition:

| Ingredient | Minimum Percentage | Maximum Percentage |
|---|---|---|
| Aloe Vera | 25 | 75 |
| Citric Acid | 0.2 | 2 |
| Potassium Sorbate | 0.1 | 2 |
| Sodium Benzoate | 0.1 | 2 |
| Cornstarch | 0.5 | 69.5 |
| Cosmetic Clay | 0.5 | 69.5 |
| Albumin | 1 | 10 |
| Hydroxypropylmethylcellulose | 0.5 | 10 |
| Allantoin | 0.5 | 5 |
| [Retinol] Vitamin A | 0.1 | 5 |
| [Ergocalciferal] Vitamin $D_2$ | 0.1 | 5 |
| [Tocopherol] Vitamin E | 0.1 | 5 |

* * * * *